July 7, 1970 E. S. BOERNER Plant Pat. 2,980
ROSE PLANT
Filed Sept. 23, 1968
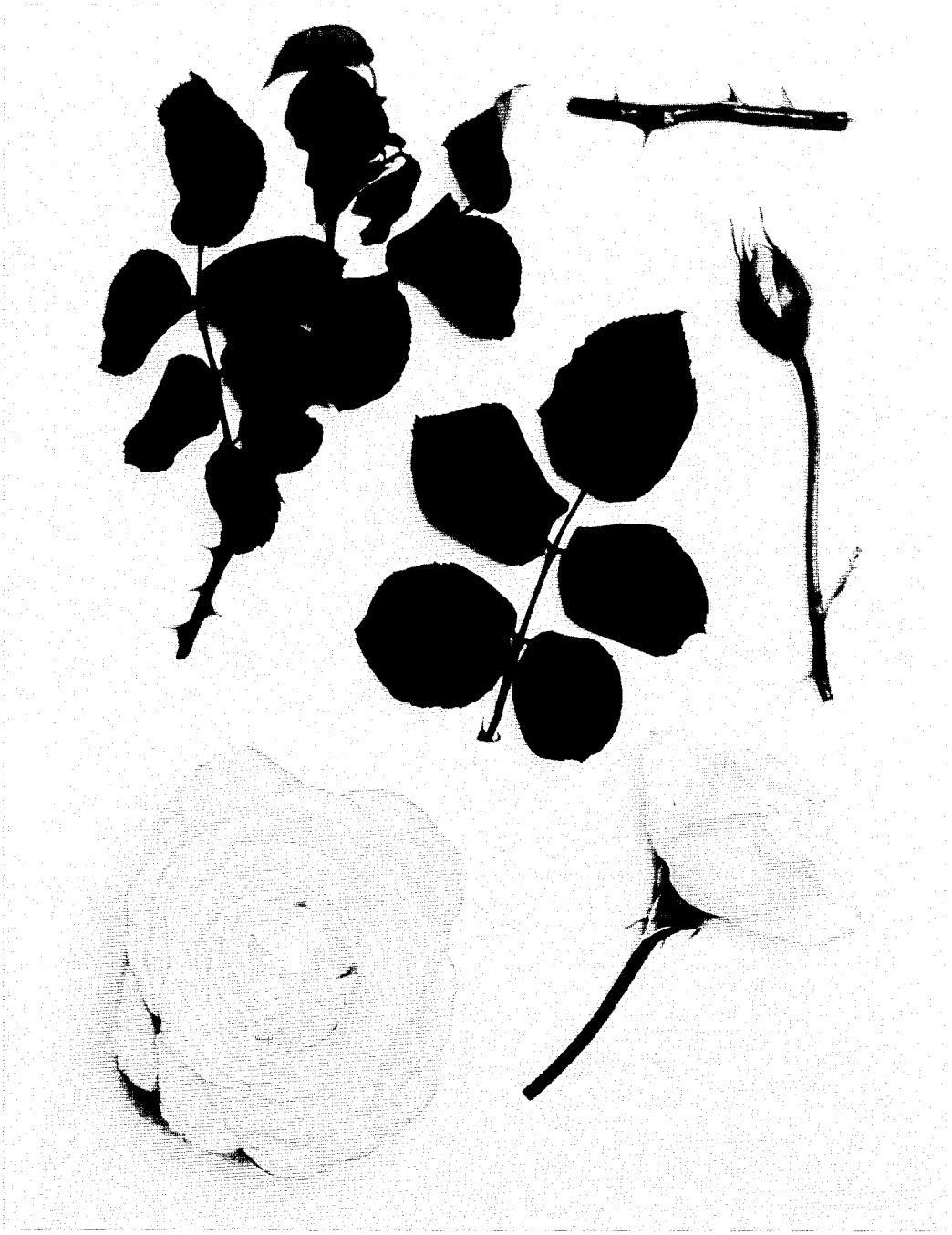
Inventor.
E. S. Boerner, Deceased
By: Lincoln Rochester Trust Company
By: Edward L. Jenner, Trust Officer
and Roger L. Boerner, Executors
By: Robb & Robb, Attorneys.

United States Patent Office

Plant Pat. 2,980
Patented July 7, 1970

2,980
ROSE PLANT

Eugene S. Boerner, deceased, late of Benton, N.Y., by Lincoln Rochester Trust Company, New York, N.Y., and Roger L. Boerner, Milwaukee, Wis., executors, assignors to Jackson & Perkins Company, Newark, N.Y., a corporation of New York

Filed Sept. 23, 1968, Ser. No. 763,990
Int. Cl. A01h *5/00*
U.S. Cl. Plt.—11 1 Claim

The present invention relates to a new and distinct variety of rose plant of the hybrid tea class, which was originated by the late Eugene S. Boerner, deceased, by crossing the rose variety known as "Kordes' Perfecta" (Plant Pat. No. 1,604) with an unnamed and unpatented seedling of the rose variety known as "Garnette Supreme" (Plant Pat. No. 1,318).

The primary objective of this breeding was to produce a new and improved rose variety having an unusual flower color, combined with good floriferousness. This objective was fully achieved, along with other desirable features, as evidenced by the following unique combination of characteristics which are outstanding in the new variety, and which distinguish it from its parents, as well as from all other rose varieties:

(1) An upright and vigorous plant habit; (2) Above average freedom of bloom; and (3) A distinctive, attractive and unique pink flower color.

While the plant habit of the new variety is vigorous like that of the parent variety "Kordes' Perfecta," the flower color differs from that of either parent and from all other rose varieties.

Asexual reproduction of the new variety by budding, as performed at Newark, N.Y., and also at Pleasanton, Calif., shows that the aforementioned characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature except where general color terms of ordinary dictionary significance are obvious:

Parentage: Seedling.
- *Seed parent.*—"Kordes' Perfecta."
- *Pollen parent.*—An unnamed seedling of "Garnette Supreme."

Class: Hybrid tea.

FLOWER (Observations made from specimens grown outdoors at Newark, N.Y. in the early afternoon during the month of August.)

Blooming habit: Above average freedom of bloom. Continuity—continuous.

Bud:
- *Peduncle.*—Relatively heavy. Size—from 2½ inches to 3 inches long. Prickles—many; small; color—Biscay Green, Plate 17.
- *Before calyx breaks.*—Size—about 1 inch long. Shape—oval, with pointed tip. Color—Biscay Green, Plate 17, with margins often suffused with Claret Brown, Plate 1.
- *Sepals (as calyx breaks).*—Color—Biscay Green, Plate 17, suffused on some margins with Claret Brown, Plate 1, and edges having few long, narrow appendages and very few gland-like hairs.

- *Petal color (as sepals separate).*—Rose Red, Plate 12.

Bloom:
- *Opening flower.*—Shape—broadly oval, with pointed tip; early opening petals spiral shaped.
- *Open flower.*—Shape—high-centered; some center petals strongly incurved. Size—from 3½ inches to 4½ inches in diameter; overall shape nearly round.
- *Petals.*—Shape: inner petals—oval; narrow base; broad near tip; outer petals—broadly oval; rounded or very bluntly pointed apex. Quantity—from 35 to 80 petals. Substance—average thickness and strength. Color—Newly open: Upper surface—Spinel Pink, Plate 26 on outer half, blending toward center to near white, with base of Pale Lemon Yellow, Plate 4 suffusing into the white area; lower surface—Spinel Pink, Plate 26, blended with white over entire surface, except more white near midrib. Three-days open: upper surface—Deep Rose Pink, Plate 12, mottled with Rose Pink, Plate 12, and blending to near white at lower end of petal, with petal base Pale Lemon Yellow, Plate 4.
- *Petaloids.*—Hang on for 3 to 5 days and then drop off cleanly.

REPRODUCTIVE ORGANS

Stamens: Numerous; arranged orderly around receptacle.
Filaments: Uneven length. Color—Light Cadmium Yellow, Plate 4.
Anthers: Large. Color—Light Cadmium Yellow, Plate 4.
Stigmas: Color—Baryta Yellow, Plate 4.
Styles: Enlarged just below stigmas. Color—enlarged part is Scarlet Red, Plate 1, and lower part is Baryta Yellow, Plate 4.

PLANT

Habit: Upright; freely branched; average size when mature.

Foliage:
- *Leaves.*—Compound of 5–7 leaflets.
- *Leaflets.*—Shape—broadly elliptical. Edge—doubly and irregularly serrated and irregularly undulated. Color (upper surface)—Forest Green, Plate 17. Surface—leathery; non-glossy.
- *Rachis.*—8 or more large thorns on lower side, with numerous smaller prickles, extending into midribs of leaflets.
- *Stipules.*—Narrow; edges with many gland-like hairs; points long, slender and parallel with rachis.

Stems:
- *Color (with flowers developed).*—Light Elm Green, Plate 17 on sunny side, shading to Courge Green, Plate 17 on shady side.
- *Old wood.*—Color—Biscay Green, Plate 17.
- *Surface.*—Smooth.

New growth: Color—Diamine Brown, Plate 13.
Thorns: Long base, with points angled downward; small thorns have oval base and are angled nearly 90° from stems. Color: large thorns—Old Gold, Plate 16; small thorns—Chestnut, Plate 2.

What is claimed is:

1. A new and distinct variety of rose plant of the hybrid tea class, substantially as herein shown and described, characterized particularly as to novelty by the unique combination of an upright and vigorous plant habit, above average freedom of bloom, and a distinctive, attractive and unique pink flower color.

No references cited.

ROBERT E. BAGWILL, Primary Examiner